(12) United States Patent
Karthikeyani et al.

(10) Patent No.: US 10,130,943 B2
(45) Date of Patent: Nov. 20, 2018

(54) CATALYST COMPOSITION FOR FLUID CATALYTIC CRACKING, PROCESS FOR PREPARING THE SAME AND USE THEREOF

(71) Applicant: INDIAN OIL CORPORATION LIMITED, Mumbai, Maharashtra (IN)

(72) Inventors: Arumugam Velayutham Karthikeyani, Faridabad (IN); Mohan Prabhu Kuvettu, Faridabad (IN); Biswanath Sarkar, Faridabad (IN); Pankaj Kumar Kasliwal, Faridabad (IN); Balaiah Swamy, Faridabad (IN); Ganga Shankar Mishra, Faridabad (IN); Kamlesh Gupta, Faridabad (IN); Santanam Rajagopal, Faridabad (IN); Ravinder Kumar Malhotra, Faridabad (IN); Kumar Brijesh, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 408 days.

(21) Appl. No.: 14/414,419

(22) PCT Filed: Jul. 23, 2013

(86) PCT No.: PCT/IB2013/056025
§ 371 (c)(1),
(2) Date: Jan. 12, 2015

(87) PCT Pub. No.: WO2014/016764
PCT Pub. Date: Jan. 30, 2014

(65) Prior Publication Data
US 2015/0190794 A1 Jul. 9, 2015

(30) Foreign Application Priority Data

Jul. 24, 2012 (IN) .......................... 2120/MUM/2012

(51) Int. Cl.
*B01J 29/06* (2006.01)
*B01J 29/80* (2006.01)
(Continued)

(52) U.S. Cl.
CPC .............. *B01J 29/80* (2013.01); *B01J 21/12* (2013.01); *B01J 21/16* (2013.01); *B01J 23/10* (2013.01); *B01J 29/088* (2013.01); *B01J 29/166* (2013.01); *B01J 29/40* (2013.01); *B01J 29/405* (2013.01); *B01J 35/0006* (2013.01); *B01J 35/08* (2013.01); *B01J 37/0009* (2013.01); *B01J 37/0045* (2013.01); *B01J 37/04* (2013.01); *B01J 37/28* (2013.01); *C07C 4/06* (2013.01); *C10G 11/04* (2013.01); *C10G 11/18* (2013.01); *B01J 21/08* (2013.01); *B01J 23/36* (2013.01); *B01J 29/084* (2013.01); *B01J 29/65* (2013.01); *B01J 29/7034* (2013.01); *B01J 29/7042* (2013.01); *B01J 29/7046* (2013.01); *B01J 35/1061* (2013.01); *B01J 2029/062* (2013.01); *B01J 2029/081* (2013.01); *B01J 2229/20* (2013.01); *B01J 2229/42* (2013.01); *C07C 2529/076* (2013.01); *C07C 2529/08* (2013.01); *C07C 2529/16* (2013.01); *C07C 2529/40* (2013.01); *C07C 2529/48* (2013.01); *C07C 2529/80* (2013.01); *C07C 2529/85* (2013.01);
(Continued)

(58) Field of Classification Search
CPC . B01J 29/40; B01J 29/80; B01J 29/088; B01J 29/084; B01J 29/405; B01J 29/48; B01J 29/081; B01J 29/166; B01J 2229/20; B01J 2229/42; B01J 2029/062; B01J 37/04; B01J 37/0045; B01J 37/0009; B01J 37/28; B01J 35/0006; B01J 35/08; B01J 2029/081; C07C 2529/40; C07C 2529/80; C07C 2529/08; C07C 2529/076; C07C 2529/16; C07C 2529/48
USPC ......... 502/63, 64, 65, 67, 68, 69, 71, 77, 79
See application file for complete search history.

(56) References Cited

U.S. PATENT DOCUMENTS 4,980,053 A 12/1990 Li et al.
5,055,176 A 10/1991 Herbst et al.
(Continued)

FOREIGN PATENT DOCUMENTS

EP 0489324 A1 6/1992
EP 2298445 A1 3/2011
WO 00/31215 A1 6/2000

OTHER PUBLICATIONS

Ishihara et al., "Large Mesopore Generation in an Amorphous SiliC-Alumina by Controlling the Pore Size with the Gel Skeletal Reinforcement and Its Application to Catalytic Cracking", Catalysts, 2012, 2, 368-385.*
(Continued)

*Primary Examiner* — Elizabeth D Wood
(74) *Attorney, Agent, or Firm* — Maschoff Brennan

(57) ABSTRACT

The present invention provides a catalyst composition for use in a catalytic cracking process, said catalyst composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component, the percentage being based on weight of the catalyst composition. The present invention also provides a process for preparing the said catalyst composition and a catalytic cracking process comprising contacting the said catalyst composition with a feedstock.

9 Claims, No Drawings

(51) Int. Cl.
*B01J 29/40* (2006.01)
*B01J 37/00* (2006.01)
*B01J 29/16* (2006.01)
*B01J 37/28* (2006.01)
*B01J 35/08* (2006.01)
*B01J 37/04* (2006.01)
*B01J 21/12* (2006.01)
*B01J 21/16* (2006.01)
*C10G 11/18* (2006.01)
*C10G 11/04* (2006.01)
*B01J 23/10* (2006.01)
*B01J 29/08* (2006.01)
*B01J 35/00* (2006.01)
*C07C 4/06* (2006.01)
*B01J 21/08* (2006.01)
*B01J 23/36* (2006.01)
*B01J 29/65* (2006.01)
*B01J 29/70* (2006.01)
*B01J 35/10* (2006.01)

(52) U.S. Cl.
CPC ..... *C10G 2300/70* (2013.01); *C10G 2400/02* (2013.01); *C10G 2400/04* (2013.01)

(56) References Cited

U.S. PATENT DOCUMENTS

| | | | |
|---|---|---|---|
| 5,326,465 A | 7/1994 | Yongqing et al. | |
| 5,380,690 A * | 1/1995 | Zhicheng | B01J 29/40 502/65 |
| 5,846,402 A * | 12/1998 | Mandal | B01J 29/80 208/113 |
| 5,965,474 A * | 10/1999 | Balko | B01J 29/005 208/113 |
| 7,033,487 B2 * | 4/2006 | O'Connor | B01J 21/16 208/113 |
| 7,375,256 B2 * | 5/2008 | Xie | C07C 4/06 585/649 |
| 7,691,768 B2 | 4/2010 | Lau et al. | |
| 2007/0060780 A1 | 3/2007 | Stamires et al. | |
| 2007/0119750 A1 * | 5/2007 | Nonaka | B01J 21/04 208/208 R |
| 2007/0209969 A1 | 9/2007 | Shen et al. | |
| 2008/0093263 A1 * | 4/2008 | Cheng | B01J 29/80 208/114 |
| 2009/0057199 A1 * | 3/2009 | Ziebarth | B01D 53/8628 208/122 |
| 2010/0276337 A1 * | 11/2010 | Yaluris | B01D 53/8628 208/113 |
| 2012/0118793 A1 * | 5/2012 | Hoffer | B01J 23/8892 208/120.2 |

OTHER PUBLICATIONS

Falco et al., "Accessibility in alumina matrices of FCC catalysts", Applied Catalysis A: General 315 (2006), 29-34.*
Kumar et al., "Control of mesoporosity in alumina", Indian Journal of Chemical Technology, vol. 8, May 2001, 157-161.*
Stockwell et al., "Distributed Matrix Structures—novel technology for high performance in short contact time FCC", Studies in Surface Science and Catalysis, vol. 149, 2004, 257-285.*

* cited by examiner

CATALYST COMPOSITION FOR FLUID CATALYTIC CRACKING, PROCESS FOR PREPARING THE SAME AND USE THEREOF

FIELD OF INVENTION

The present invention relates to a catalyst composition for use in a catalytic cracking process. More particularly, the present invention provides a metal tolerant catalyst composition for fluid catalytic cracking of heavy petroleum feed for enhancing yield of olefins. The present invention also relates to a process for preparing the catalyst and manner of use thereof.

BACKGROUND OF INVENTION

Fluid catalytic cracking is an important process used in petroleum refineries for converting heavy feed into lighter products namely gasoline, diesel and liquefied petroleum gas (LPG). Processing of heavy feeds is becoming more significant because of cost reasons. However, processing of heavy feeds is difficult because of higher amounts of Conradson Carbon Residue (CCR) and poisonous metals such as nickel and vanadium.

In general in the catalytic cracking process, metal trap agents are added to the catalyst during its manufacturing process as a part of catalyst formulation or added as separate additive particles, or added to feed during processing step to handle feed metals and get maximum liquid petroleum gas and propylene yield of 25 wt % and 10 wt % on fresh feed basis.

U.S. Pat. No. 5,846,402 discloses a single catalyst component system comprising ultra-stable Y (USY) zeolite (1-6 wt %), shape selective pentasil zeolite (8-25 wt %), bottom selective active material (0-8 wt %), rare earth component (0-1 wt %) and non-acidic components and binder (91-60 wt %). It is used for enhancing ethylene, liquid petroleum gas, propylene and other olefins of heavy hydrocarbon feed stock such as mixed vacuum gas oil, Visbreaker (VB) tar, solvent deasphalted oil and paraffinic vacuum gas oil. The metal tolerance of the catalyst system is tested with the metal level of vanadium of around 20,000 ppm. It enhances the yield of LPG, propylene and other olefins.

U.S. Pat. No. 5,380,690 discloses another single catalyst/component system comprising clay (0-70 wt %), inorganic oxides (5-99 wt %), zeolite (1-50 wt %). The zeolite in the catalyst is a mixture of 0-25 wt % of Rare Earth Exchanged Y (REY)/high Silica Y zeolite & 75-100 wt % of phosphorus and rare earth containing high silica zeolite having a structure of pentasil, for enhancing ethylene, propylene and other olefins production in the feedstock. The feedstock consists of vacuum oil (0.881 gm/cc). The performance of the catalyst system is evaluated without metals.

U.S. Pat. No. 7,375,256 describes a catalyst comprising of phosphorous and transition metal modified silica rich zeolite, wherein said transition metal is at least one element selected from the group consisting of Fe, Co, Ni, Cu, Zn, Mo and Mn having a structure of pentasil in a riser or a fluidized bed reactor. The catalyst composition increases the yield of ethylene, propylene and other olefins in the feed stock of vacuum gas oil (VGO) (0.873 gm/cc) & paraffin based atmospheric residual oil (0.896 gm/cc). The performance of the catalyst system is also evaluated without metals.

U.S. Pat. No. 7,691,768 discloses a catalyst mixture comprising ECAT (100%), ECAT (96%)+commercial additive (4%) (K-2000), ECAT (96%)+Commercial additive (4%) ($Re_2O_3$ 6C). Further, it also contains 6% p/p of the rare earth precipitated into the zeolite. It was evaluated in the feedstock of Heavy Gas oil (HGO) having density—0.852 g/cm$^3$) and RCR –0.43% p/p, for enhancing the yield of LPG and propylene in the feedstock. However, the patent does not mention about presence and tolerance with respect to any metals in the feedstocks.

Solid acidic catalyst described in U.S. Pat. No. 4,980,053, is selected from the group consisting of pentasil shape selective molecular sieves, Ultra-stable hydrogen Y sieves, and a mixture of Ultra-stable hydrogen Y sieves and pentasil shape selective molecular sieves. It comprises of CHO-Pentasil+REY, ZCO-USY, CHP-Pentasil shape selective molecular sieve supported on kaolinite, and LWC II-amorphous alumino silicate catalyst used to increase the yield of ethylene and propylene. The feedstock for the catalyst includes vacuum gas oil VGO (0.873 gm/cc), Straight Run Naphtha (SRN), residual oil (RO). However, the presence of any metal on the catalyst is not mentioned.

U.S. Pat. No. 5,055,176 mentions a cracking catalyst comprising catalytically effective amounts of a large pore molecular sieve (5-50 wt %), a shape selective zeolite having paraffin cracking/isomerization activity (0.1-20 wt %), a shape selective zeolite having paraffin aromatization activity (0.1-20 wt %), and a matrix, used to increase ethylene and propylene. However, the metal tolerance of the catalyst is not disclosed.

U.S. Pat. No. 5,326,465 describes a solid acidic catalyst comprising rare-earth containing high silica zeolite having the structure of a 10-40% pentasil (ZRP), REY and high Silica Y zeolite which is used to crack the feedstock such as SRN, LGO, VGO and residues CCR (0.22-3.81) and for improving the yield of LPG, propylene and other olefins. The catalyst system is tested with metal containing only Nickel, but no vanadium.

In light of the prior art processes, there exist a need for developing a catalyst composition for maintaining a high LPG and propylene selectivity, such that the same can handle higher amounts of metal contaminants and higher CCR with high metal tolerance.

SUMMARY OF INVENTION

Accordingly, the present invention provides a catalyst composition that can effectively treat feed stocks to get high LPG, ethylene and propylene selectivity. The catalyst composition provides for the high selectivity even when the catalyst carries an equilibrium nickel concentration in excess of 5000 ppm and an equilibrium vanadium concentration in excess of 10000 ppm. Also, the catalyst composition is capable of processing heavy feeds having high amounts of nickel and vanadium.

More particularly, the present invention provides a catalyst composition for use in a catalytic cracking process, said catalyst composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component, the percentage being based on weight of the catalyst composition.

The present invention also provides a process for preparing catalyst composition comprising mixing a source of pentasil zeolite, a source of ultra-stable Y (USY) or rare earth exchanged USY (REUSY) zeolite, a source of large pore active matrix based bottom up gradation component and a source of a metal trap component such that the composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component.

The present invention further provides a catalytic cracking process comprising contacting a catalyst composition with a feedstock comprising Coker gasoline, Coker Fuel Oil (CFO), hydro cracker bottom, Vacuum Gas Oil (VGO), Heavy Vacuum Gas Oil (HVGO), Vacuum Residue, Residue Coker Oil (RCO), Once Through Hydrocracker Unit Bottom (OHCUB) and mixtures thereof under a fluid catalytic cracking condition so as to obtain a cracked product comprising dry gas and LPG, said dry gas comprising 33 to 75% of ethylene & said LPG comprising 25 to 63% of propylene, wherein the catalyst composition comprises 3.5 to 15.5% of pentasil zeolite, 9 to 40% of ultra-stable Y zeolite (USY) or rare earth exchanged USY (REUSY) zeolite, 3.5 to 15% of large pore active matrix based bottom up gradation component and 0.3 to 3% of a metal trap component.

The above and other aspects of the present invention are further attained and supported by the following embodiments described herein. However, the described embodiments are in accordance with the best mode of practice and the scope of the invention is not restricted to the described embodiments herein after.

DETAILED DESCRIPTION OF INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The catalyst composition of present invention is mainly used for enhancing olefin yield i.e. ethylene, propylene & LPG from heavy hydrocarbon feed stock. The catalyst composition is used to enhance olefin yield during fluid catalytic cracking (FCC). The feedstock includes Coker gasoline, Coker Fuel Oil (CFO), hydro cracker bottom, Vacuum Gas Oil (VGO), Heavy Vacuum Gas Oil (HVGO), Vacuum Residue, Residue Coker Oil (RCO), Once Through Hydrocracker Unit Bottom (OHCUB) and mixtures thereof. The catalyst composition is metal tolerant and is functional at high concentration of metals.

The catalyst composition according to the invention is used for conversion of hydrocarbon feed streams containing high concentrations of metals more specifically, nickel, vanadium, iron & sodium and CCR, employing the metal tolerant catalyst composition of the invention to get more LPG and propylene by maintaining its activity and selectivity in a continuous circulating fluidized bed reactor-regenerator unit.

According to this invention, there is provided a process for upgrading LPG, propylene and ethylene in the presence of the catalyst composition of the present invention. The catalyst composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component. The aforesaid ingredients of the catalyst composition interact in a synergistic manner among themselves. Also, the catalyst composition is very much dependent on the type of feedstock to be processed.

Accordingly, the present invention provides a catalyst composition for use in a catalytic cracking process, said catalyst composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component, the percentage being based on weight of the catalyst composition.

In one embodiment of the present invention, the catalyst composition comprises pentasil zeolite preferably in range of 4 to 8%, ultra stable Y (USY) or rare earth exchanged USY (REUSY) zeolite preferably in the range of 10 to 25%, large pore active matrix based bottom up gradation component preferably in the range of 6 to 15% and metal trap component preferably in range of 0.4 to 3%.

In an embodiment of the present invention, the pentasil zeolite has a pore size in the range of $5.1°$ A to $5.6°$ A and is selected from a group comprising of ZSM-5 Zeolite, ZSM-11 Zeolite, ZSM-12 Zeolite, ZSM-22 Zeolite, ZSM-23 Zeolite, and ZSM-35 Zeolite.

In another embodiment of the present invention, the REUSY zeolite comprises 3 to 5 wt. % of a rare earth cation selected from a group comprising of rhenium, lanthanum, cerium, praseodymium, neodymium, samarium and gadolinium.

In yet another embodiment of the present invention, the large pore active matrix based bottom up gradation component comprises alumina.

In still an embodiment of the present invention, the large pore active matrix based bottom up gradation component has a pore size in the range of $80°$ A to $200°$ A.

In yet another embodiment of the present invention, the metal trap component comprises at least one of a vanadium trap component and a nickel trap component wherein said vanadium trap component is selected from a group comprising of phosphorus, aluminium, lanthanum, cerium, rhenium, praseodymium, neodymium, samarium, gadolinium, tin, strontium, titanium, zirconium and silicon; and said nickel trap component is selected from a group comprising of cerium, antimony, bismuth, phosphorus, aluminium and silicon.

In still another embodiment of the present invention, a remaining amount of catalyst composition is comprised of a binder and filler.

In one embodiment of the present invention, the binder is selected from a group comprising of alumina, silica, silica-alumina and phosphate.

In still another embodiment of the present invention, the filler is selected from a group comprising of kaolin clay, montmorillonite clay, bentonites clay, laolinite clay and halloysite clay, aluminum trihydrate, bayerite, and gamma alumina.

In yet another embodiment of the present invention, the catalyst composition is in the form of a composite catalyst or as a mixture of additives.

Further, the present invention provides a process for preparing a catalyst composition for use in a catalytic cracking process, said process comprises mixing a source of pentasil zeolite, a source of ultra-stable Y (USY) or rare earth exchanged USY (REUSY) zeolite, a source of large pore active matrix based bottom up gradation component and a source of a metal trap component, wherein an amount of source of pentasil zeolite, the source of ultra-stable Y (USY) or rare earth exchanged USY (REUSY) zeolite, the source of large pore active matrix based bottom up gradation component and the source of a metal trap component is such that the composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component. Particularly, the catalyst composition comprises pentasil zeolite preferably in range of 4 to 8%, USY or REUSY zeolite preferably in the range of 10 to 25%, large pore active matrix based bottom up gradation component preferably in the range of 6 to 15% and metal trap component preferably in range of 0.4 to 3%.

Further, the present invention also provides a catalytic cracking process comprises contacting a catalyst composition with a feedstock comprising Coker gasoline, Coker Fuel Oil (CFO), hydro cracker bottom, Vacuum Gas Oil (VGO), Heavy Vacuum Gas Oil (HVGO), Vacuum Residue, Residue Coker Oil (RCO), Once Through Hydrocracker Unit Bottom (OHCUB) and mixtures thereof under a fluid catalytic cracking condition so as to obtain a cracked product comprising dry gas and LPG, said dry gas comprising 33 to 75% of ethylene & said LPG comprising 25 to 63% of propylene, wherein the catalyst composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component.

The present invention, provides a catalyst composition comprising of medium pore pentasil zeolite in an amount in the range of 3.5 to 15.5 wt %, ultra-stable Y (USY)/rare earth exchanged USY (REUSY) zeolite and their mixture in an amount in the range of 9 to 40 wt %, large pore active matrix based residue upgradation component in an amount in the range of 3.5 to 15 wt %, active metal trap component in an amount in the range of 0.3 to 3 wt %. The catalyst composition is prepared as composite catalyst or as mixture of additives, capable of cracking heavier hydrocarbons with total metals ranging from 5-200 ppm & CCR upto 10 wt % with metal tolerance upto 30,000 ppm. The catalyst composition is capable of producing LPG and propylene from heavier hydrocarbons up to 50 wt % & 27 wt % respectively on fresh feed basis.

In the present invention the activity and selectivity of the catalyst composition is governed by residue upgrading component, USY/REUSY zeolite, medium pore pentasil zeolite and metal trap component. The residue upgrading component according to the invention, facilitates cracking of large hydrocarbon molecules to smaller one that are then accessible to the USY/REUSY zeolite. It improves bottom reduction by cracking the larger molecules in the bottom fraction. It also partially improves metal resistant of the catalyst by cracking the heavy-metal containing molecules and binding some of the metals such as vanadium to the pseudoboemite component. According to the current invention USY/REUSY zeolite is used and it along with the residue upgrading component selectively cracks heavy hydrocarbons to give maximum middle distillates. The middle distillates molecules will be further cracked by pentasil zeolite to maximize propylene rich LPG.

The catalyst composition with the specially designed USY/REUSY zeolite and residue upgrading component in the aforesaid weight percentage plays a key role in the performance of current invention, i.e. at constant catalyst activity, decrease in USY/REUSY zeolite to residue upgrading component results in an increase in LCO (Light Cycle Oil), coke, dry gas yields, increase in olefin in LPG and a decrease in bottom yield.

At the same time, cracking of heavy residue feedstock requires a catalyst with low coke selectivity. An increase in the amount of the medium pore pentasil zeolite to residue upgradation additive will reduce catalyst coke selectivity. The medium pore pentasil zeolite present in the present invention not only increases the propylene selectivity, but it also increases the coke selectivity (less coke yield) as pore size of pentasil is small and there is no space for cyclization reaction to proceed.

According to the current invention, for handling heavier hydrocarbons having 10 wt % CCR and metal (Ni & V) 200 ppm, the use of metal trap component as a fourth component helps to maintain the zeolite activity to increase gasoline yield and reduce yields of hydrogen and coke.

Therefore, a balanced amount of each of Y-zeolite component, residue up-gradation additive, pentasil zeolite component and metal trap component is prepared to achieve the desired catalytic activity. It may be noted that depending on feedstock composition, process parameters and desired product state, wt % of each of USY/REUSY, residue upgradation additive, pentasil zeolite and metal trap component can be varied within the aforesaid range of wt %.

In accordance with an embodiment of the present invention, the catalyst composition in the present invention is prepared in the form of composite catalyst or as a mixture of additives comprising medium pore pentasil zeolite in an amount in the range of 3.5 to 15.5 wt %, ultra stable Y (USY)/rare earth exchanged USY (REUSY) zeolite and their mixture in an amount in the range of 9 to 40 wt %, large pore active matrix based residue upgradation component in an amount in the range of 3.5 to 15 wt %, active metal trap component in an amount in the range of 0.3 to 3 wt %. The catalyst system is capable of having metal tolerance Ni (500 ppm-10000 ppm) & V-(1000 ppm-20000 ppm) and exhibits enhanced propylene yield up to ~27 wt % using VGO feed stock and ~16 wt % using heavy feed stock, on fresh feed basis by maintaining its activity and selectivity in a continuous circulating fluidized bed reactor-regenerator unit.

Feed Stocks:

Feed stock for the present invention includes a wide range of hydrocarbon fractions starting from light fractions to heavy fractions such as Coker gasoline, CFO, VGO, hydro cracker bottom, Vacuum Residue, RCO, HVGO, OHCUB and their mixtures, etc. The feed stocks used in this invention are the residual fractions having metals (Ni+V) more than 40 ppm. Table-1 gives the properties of feed stock used in this invention.

TABLE 1

| Feed Properties | Unit | Coker Gasoline (CG) | Coker Fuel Oil (CFO) | Once through hydro cracker unit bottom (OHCUB) | Vacuum gas oil (VGO) | Residue Coker Oil (RCO) | Mixed feed (CG:CFO:RCO) | Vacuum Residue (VR) |
|---|---|---|---|---|---|---|---|---|
| Density @ 15 C. | gm/cc | 0.717 | 0.926 | 0.838 | 0.88 | 0.946 | 0.928 | 0.9053 |
| CCR | wt % | — | 0.15 | 0.05 | 0.5 | 5.86 | 2.91 (3) | 10.37 |
| Vanadium | ppm | <0.1 | — | — | <1 | <1 | — | 51 |

TABLE 1-continued

| Feed Properties | Unit | Coker Gasoline (CG) | Coker Fuel Oil (CFO) | Once through hydro cracker unit bottom (OHCUB) | Vacuum gas oil (VGO) | Residue Coker Oil (RCO) | Mixed feed (CG:CFO:RCO) | Vacuum Residue (VR) |
|---|---|---|---|---|---|---|---|---|
| Nickel | ppm | <1 | — | — | <1 | <1 | — | 15 |
| Sulfur | wt % | — | — | — | 0.5 | — | — | 2.48 |
| Paraffin | wt % | — | — | — | — | — | 46.8 | 43.2 |
| Naphthene | wt % | — | — | — | — | — | 21.6 | 20.0 |
| Aromatics | wt % | — | — | — | — | — | 31.6 | 36.50 |
| Distillation | | | | | | | | |
| IBP | °C. | 39 | 242 | — | 327 | — | — | — |
| 95% | °C. | 126 | >400 | | 526 | | | |
| FBP | °C. | 153 | | | 545 | | | |

Catalysts:

The catalyst composition employed in this invention includes four active ingredients namely medium pore pentasil zeolite in an amount in the range of 3.5 to 15.5 wt %, ultra stable Y (USY)/rare earth exchanged USY (REUSY) zeolite and their mixture in an amount in the range of 9 to 40 wt %, large pore active matrix based residue upgradation component in an amount in the range of 3.5 to 15 wt %, active metal trap component in an amount in the range of 0.3 to 3 wt %. Also, the catalyst composition can be in the form of composite catalyst or as a mixture of additives. In case, the catalyst composition in the form of a mixture of additive, there can be 4 additives namely:
1. USY/REUSY zeolite based additive which comprises USE/REUSY zeolite;
2. Pentasil zeolite based additive which comprises pentasil zeolite;
3. Residue upgradation additive which comprises residue upgradation component; and
4. Metal trap additive which comprises metal trap component.

The catalyst composition can be prepared from the aforesaid additives by mixing together all the said four additives after each additive has been separately prepared. The additives can be mixed in varying quantities depending upon the wt % of the active ingredient in each additive.

In the following paragraphs, a brief explanation on the process for preparing USY/REUSY zeolite based additive, Pentasil zeolite based additive, Residue upgradation additive and metal trap additive is provided.

USY/REUSY Zeolite Based Additive:

US/REUSY zeolite based additive is prepared by incorporating 20-50 wt % ultra-stable Y (USY) or a rare earth exchanged USY (REUSY) zeolite into or with active silica-alumina binder and filler material (such as clay). The additive is prepared based on the technique (high dispersion of REUSY zeolite in to the silica-alumina matrix) as described in the U.S. Pat. No. 6,528,447 and incorporated herein by reference. The active silica-alumina binder is designed in such a way that it cracks the heavier hydrocarbon molecules and provides a low resistance path for molecular diffusion so that the cracked hydrocarbons are easily available for further cracking in to the zeolite. The final slurry with solid concentration ranging from 25-35 wt % is spray dried at an inlet temperature of 350-400° C. and at an outlet temperature of 120-140° C. to get the micro spheroidal particle having Average Particle Size (APS) of 80-110 micron suitable for FCCU operation.

In another embodiment the Y-zeolite based additive comprises ultra-stable Y (USY) or rare earth exchanged USY (REUSY) zeolite or a mixture of both in an amount in the range of 20 to 50 wt %. The balance wt % is constituted by the active silica-alumina binder and the filler material.

In case the Y zeolite based additive comprises REUSY zeolite, the same can contain 3-5 wt % of rare earth and preferably, 3.8-4 wt % of rare earth.

Pentasil Zeolite Based Additive:

Pentasil zeolite based additive (ZSM-5 additive) is prepared by incorporating 5-50 wt % pentasil zeolite, 1-15 wt % alumina, 5-20 wt % silica, $PO_4$ of 5-20 wt % and 20-60 wt % of kaolin clay. This zeolite is treated with phosphate so that its maximum activity is retained in the additive. The phosphated zeolite is mixed with active binder prepared with judicial combination of Silica-alumina-clay-phosphate materials so that its key physical properties for fluidization in FCC unit such as Apparent Bulk Density (ABD), Attrition Index (AI) and Average Particle Size (APS) can be maintained. The final slurry with solid concentration ranging from 35-42 wt % is spray dried at an inlet temperature of 350-400° C. and at an outlet temperature of 120-140° C. to get the micro spheroidal particle having APS of 80-110 micron suitable for FCCU operation.

The pore size of medium pore pentasil zeolite is in the range of 5.1-5.6°A. The ZSM-5 additive comprises 5-50 wt % pentasil zeolite, 1-15 wt % alumina, 5-20 wt % silica, $PO_4$ of 5-20 wt % and 20-60 wt % of kaolin clay.

Residue Upgradation Additive:

Residue upgradation additive slurry was prepared by using supplementary binder based on silica-alumina with different pore size and different phosphate as coke retarding material. Initially alumina gel was prepared by addition of formic acid and mixed with clay-phosphate-silica binder and slurry prepared with solid concentration ranging from 25-35 wt %. The final slurry with solid concentration ranging from 25-35 wt % is spray dried at an inlet temperature of 350-400° C. and at an outlet temperature of 120-140° C., to get the micro spheroidal particle having APS of 80-110 micron suitable for FCCU operation. Alumina which is the residue upgradation component can preferably be PSB alumina.

The pore size of large pore active matrix based residue up-gradation components is in the range of 80-200° A and most preferred range in the 100-125° A. The large pore active matrix based residue up-gradation components comprises 40-60% alumina, Silica 5-25%, clay 20-60% & $PO_4$ 1-20%.

Metal Trap Additive:

Metal trap additive slurry was prepared by using supplementary binder silica-alumina along with metal passivation component $Re_2O_3$. Alumina gel was prepared by addition of formic acid and mixed with clay-silica binder & in this slurry Re$_2$O$_3$ was dispersed. The slurry was prepared with solid concentration ranging from 30-40 wt %. The final slurry with solid concentration ranging from 30-40 wt % is spray dried at an inlet temperature of 350-400° C. and at an outlet temperature of 120-140° C., to get the micro spheroidal particle having APS of 85-108 micron suitable for FCCU operation.

It comprises (a) a rare earth component in the range of 10 wt % to 50 wt %, (b) alumina in the range of 5 wt % to 25 wt % (c) silica in the range from 5-30 wt %, (d) molecular sieve zeolite in range 0.1-20 wt % and (e) filler clay in the range of 20 wt % to 60 wt %.

After preparing the additives independently, they are mixed to obtain the catalyst composition comprising USY/REUSY zeolite; 10 to 60 wt % of pentasil zeolite based additive which comprises pentasil zeolite; 3 to 25 wt % of residue upgradation additive which comprises residue upgradation component; and 3 to 15 wt % of metal trap additive which comprises metal trap component.

By way of a preferred embodiment as illustrated in Table 2, the catalyst composition in the form of a mixture of additive can be obtained by mixing 33.3 to 62.5 wt % of USY/REUSY zeolite based additive which comprises USY/REUSY zeolite; 20 to 32 wt % of pentasil zeolite based additive which comprises pentasil zeolite; 13.3 to 25 wt % of residue upgradation additive which comprises residue upgradation component; and 6 to 10 wt % of metal trap additive which comprises metal trap component.

TABLE 2

Range in weight percentage of ingredient in the additive, additive in catalyst and ingredient in catalyst:

| | Active component wt % in Additive | | Additive wt % in catalyst | | Active component wt % in catalyst | |
|---|---|---|---|---|---|---|
| | Range | Preferred Range | Range | Preferred Range | Range | Preferred Range |
| USY/REUSY additive | | | 30-80 | 33.3-62.5 | | |
| USY/REUSY (RE = 3-5%) | 20-50 | 30-40 | | | 9-40 | 10-25 |
| Alumina | 10-30 | 20-30 | | | | |
| Silica | 10-20 | 12-17 | | | | |
| Filler clay | 20-60 | 25-55 | | | | |
| Pentasil zeolite additive | | | 10-60 | 20-32 | | |
| ZSM-5 zeolite | 5-50 | 10-40 | | | 3.5-15.5 | 4-8 |
| Alumina | 1-15 | 3-8 | | | | |
| Silica | 5-20 | 5-15 | | | | |
| Filler clay | 20-60 | 45-55 | | | | |
| PO4 | 5-20 | 8-15 | | | | |
| Residue Upgradation Additive | | | 3-25 | 13.34-25 | | |
| Alumina | 40-60 | 45-55 | | | 3.5-15 | 6-15 |
| Silica | 5-25 | 10-20 | | | | |
| Clay | 20-60 | 25-50 | | | | |
| PO4 | 1-20 | 3-15 | | | | |
| Metal trap additive | | | 3-15 | 6-10 | | |
| Re2O3 | 10-50 | 20-30 | | | 0.3-3 | 0.4-3 |
| Alumina | 5-25 | 10-20 | | | | |
| Silica | 5-30 | 10-25 | | | | |
| Y-zeolite | 0.1-20 | 3-10 | | | | |
| Clay | 20-60 | 30-50 | | | | | medium pore pentasil zeolite in an amount in the range of 3.5 to 15.5 wt %, ultra stable Y (USY)/rare earth exchanged USY (REUSY) zeolite and their mixture in an amount in the range of 9 to 40 wt %, large pore active matrix based residue upgradation component in an amount in the range of 3.5 to 15 wt %, active metal trap component in an amount in the range of 0.3 to 3 wt %. Particularly, the catalyst composition comprises pentasil zeolite preferably in range of 4 to 8%, USY or REUSY zeolite preferably in the range of 10 to 25%, large pore active matrix based bottom up gradation component preferably in the range of 6 to 15% and metal trap component preferably in range of 0.4 to 3%.

Table 2 provided herein below provides the concentration of each ingredient in the respective additive in the form of a range and a preferred range. Also, Table 2 provides the wt % range and a preferred wt % range for mixing each of the aforesaid four additives to obtain the catalyst composition. By way of example, the catalyst composition in the form of a mixture of additive can be obtained by mixing 30 to 80 wt % of USY/REUSY zeolite based additive which comprises It should be noted that the catalyst composition can also be prepared in the form of composite catalyst by adopting a process comprising the step of mixing a source of pentasil zeolite, a source of ultra-stable Y (USY) or rare earth exchanged USY (REUSY) zeolite, a source of large pore active matrix based bottom up gradation component and a source of a metal trap component such that the composition comprises 3.5 to 15.5% of pentasil zeolite, 9 to 40% of ultra-stable Y (USY) or rare earth exchanged USY (REUSY) zeolite, 3.5 to 15% of large pore active matrix based bottom up gradation component and 0.3 to 3% of a metal trap component. Non-restrictive illustration of the aforesaid process is given below in the form of an example.

Further, the present invention is illustrated in detail by way of the following examples. The examples are given herein for illustration of the invention and are not intended to be limiting thereof.

Example 1: Composite Catalyst Composition 170.58 gm of clay (LOI=15 wt %) and 3 gm of Re$_2$O$_3$ were dissolved in 200.5 gm of DM water containing 2.5 gm tamol, 70.42 gm of PSB alumina (LOI=29 wt %) was dispersed in 211.26 gm of DM water and peptized with 16.67 gm of formic acid. This peptized alumina was added to the clay slurry to obtain clay-alumina slurry. 250 gm of ammonium polysilicate (LOI=70 wt %) was added to this clay-alumina slurry to obtain clay-alumina-silica slurry (a). 20.85 gm of diammonium hydrogen phosphate was dissolved in 59.08 gm of DM water and 45.45 gm of pentasil zeolite was added to it under stirring to prepare ZSM-5 zeolite slurry and was added to the slurry (a) and mixed thoroughly to obtain clay-alumina-silica-zeolite slurry (b) 142.05 gm of REUSY (LOI=12 wt %) zeolite was dissolved in to 184.66 gm of DM water to make REUSY zeolite slurry and was added to the slurry (b) to obtain slurry (c).

21.13 gm of PSB alumina (LOI=29 wt %) and 11.76 gm of clay (LOI=15 wt %) was dissolved in 45 gm of DM water and milled for 2 hrs to obtain clay-alumina slurry. 3 gm of formic acid was added to this clay-alumina slurry for peptization (d). 6.07 gm of phosphoric acid (85%) was added to peptized slurry (d) to obtain slurry (e). Finally 16.67 gm of ammonium polysilicate (LOI=70 wt %) was added to this slurry (e) to obtain slurry (f).

Slurry (f) was added to the slurry (c) under stirring to obtain final single component catalyst precursor slurry. The final slurry was milled for homogenization and was spray dried, calcined to obtain final catalyst. The final single particle composite catalyst contains 25 wt % Re USY zeolite, 8 wt % ZSM-5 zeolite, 13 wt % residue up-gradation component, 3 wt % metal trap component, 31 wt % filler clay and 20 wt % binder material.

Example 2: Preparation of Additives

USY/REUSY Zeolite Based Additive:

USY/REUSY zeolite based additive is prepared by incorporating 35 wt % rare earth exchanged USY zeolite (RE-USY) containing rare earth oxide in an amount of about 3.8 wt % with active silica-alumina binder and clay filler. The catalyst is prepared based on the technique (high dispersion of REUSY zeolite in to the silica-alumina matrix) as described in the U.S. Pat. No. 6,528,447 and incorporated herein by reference.

The final slurry with solid concentration ranging from 30 wt. % is spray dried at an inlet temperature of 375° C. and at an outlet temperature of 130° C. to get the micro spheroidal particle having Average Particle Size (APS) of 95 micron suitable for FCCU operation.

The composition of the USY/REUSY zeolite based additive is given below:
ReUSY zeolite: 35 wt %
Alumina: 20 wt %
Silica: 15 wt %
Filler-clay: 30 wt %

Pentasil Zeolite Based Additive:

Pentasil zeolite based additive is prepared by incorporating 25 wt % pentasil zeolite, 5 wt % alumina, 10 wt % silica and $PO_4$ of 10 wt % and 50 wt % kaolin clay. This zeolite is treated with phosphate so that its maximum activity is retained in the additive. The phosphated zeolite is mixed with active binder prepared with judicial combination of Silica-alumina-clay-phosphate materials so that its key physical properties for fluidization in FCC unit such as Apparent Bulk Density (ABD), Attrition Index (AI) and Average Particle Size (APS) can be maintained. The final slurry with solid concentration ranging from 39 wt % is spray dried at an inlet temperature of 375° C. and at an outlet temperature of 130° C. to get the micro spheroidal particle having APS of 95 micron suitable for FCCU operation.

The composition of the pentasil zeolite based additive is given below:
ZSM-5: 25 wt %;
Alumina: 5 wt %;
Silica: 10 wt %;
$PO_4$: 10 wt % and
Kaolin clay: 50 wt %.

Residue Upgradation Additive:

Residue upgradation additive slurry was prepared by using supplementary binder based on silica-alumina with different pore size and different phosphate as coke retarding material. Initially alumina gel was prepared by addition of formic acid and mixed with clay-phosphate-silica binder and slurry prepared with solid concentration ranging from 30 wt. %. The final slurry is spray dried at an inlet temperature of 375° C. and at an outlet temperature of 130° C., to get the micro spheroidal particle having APS of 95 micron suitable for FCCU operation.

The final Residue upgradation additive composition is given below:
Alumina: 50 wt %;
Silica: 15 wt %;
$PO_4$: 5 wt %; and
Clay: 30 wt %.

Metal Trap Additive:

Metal trap additive slurry was prepared by using supplementary binder silica-alumina along with metal passivation component $Re_2O_3$. Alumina gel was prepared by addition of formic acid and mixed with clay-silica binder & in this slurry $Re_2O_3$ was dispersed. The slurry was prepared with solid concentration ranging from 35 wt. %. The final slurry is spray dried at an inlet temperature of 375° C. and at an outlet temperature of 130° C., to get the micro spheroidal particle having APS of 96 micron suitable for FCCU operation.

The final metal passivator additive composition is given below:
$Re_2O_3$: 25 wt %;
Alumina: 15 wt %;
Silica: 20 wt %;
Molecular sieve zeolite: 5 wt %; and
Filler clay: 35 wt %

Example-3: Preparation of Catalyst Compositions from Additives

The individually prepared additives were mixed at different composition to crack the different type of feed stocks starting from gasoline to residue hydrocarbon molecules to achieve maximum activity and selectivity. The detail of active material composition is given in Table-3.

TABLE 3

| Catalyst | CAT-A | CAT-B | CAT-C | CAT-D |
|---|---|---|---|---|
| Y-zeolite, wt % | 10 | 24.5 | 14 | 12.25 |
| Medium pore pentasil zeolite, wt % | 6 | 8 | 6 | 6 |
| Residue up-gradation component, wt % | 9.4 | 6.5 | 13 | 13 |
| Metal trap component, wt % | 0.5 | 1.0 | 1.5 | 3.0 |

Example-4: Catalyst Compositions Pretreatment

The catalysts without metals were deactivated at the temperature of 810° C. for 5 hrs using 100% steam. The catalysts with metal were first metal doped by conventional Mitchel method (Ref: B R Mitchell "Metal contaminants of catalytic cracking" Industrial Engineering Chemistry Prod Res & Dev 209, 19, 1980) at required nickel and vanadium levels. Then samples were reduced with partial pressure hydrogen to bring the metals in reduced state and steamed at temperature of 788° C. for 3 hours using 100% steam. The steamed catalyst was subjected to activity test in Fixed Bed Auto MAT unit under the typical conditions as shown in Table 4.

TABLE 4

| Conditions | |
|---|---|
| Weight of catalyst loaded, gms | 2.5-3.5 |
| Feed Injection time, sec | 10-75 |
| Reactor temperature, ° C. | 500-650 |
| Feed rate, gm/min | 1.5-6 |

TABLE 4-continued

| Conditions | |
|---|---|
| Reaction Severity, W/F, min | 0.5-1.5 |
| WHSV, hr$^{-1}$ | 30-60 |

After the completion of the reaction, the catalyst was stripped by nitrogen for the time period of 900 seconds to remove adsorbed reaction products. Coke on catalyst is determined by in-situ regeneration with fluidized air by heating at 660° C. The gas sample is analyzed with online micro GC. The H2, C1, C2, C3, C4 and C5 lump is determined quantitatively. The liquid products are analyzed by ASTM 2887 procedure in a simulated distillation analyzer, Perkin Elmer. The percentage of the liquid products boiling in the range of gasoline (C5-150° C.), heavy naphtha (C150-216° C.), Light Cycle Oil (C-216° C.-370° C.) and Clarified Oil (370° C.+) is calculated. Carbon on catalyst was determined by online IR analyzer.

Example-5: Cracking Different Feeds by Catalyst Composition A

Catalyst CAT-A was tested without metal and steamed at 810° C./5 hrs and its activity was evaluated in Fixed bed Auto MAT unit under ROT 580° C. and the products were analyzed as per the procedure mentioned above. This example illustrate that present catalyst composition A (which is a mixture of the four additives) without metal can crack various hydrocarbon feed stocks derived from crude oil to give more LPG and propylene selectivity on fresh feed basis (Table-5). The propylene in LPG selectivity is higher with RCO and VGO feed stocks than that derived from intermediate other feed stocks such as CG, CFO and OHCUB. The ethylene selectivity in dry gas could be achieved in the range of 43-63% and propylene selectivity in LPG could be achieved around 50%.

TABLE 5

Cracking of Different feeds by Catalyst A

| Catalyst | Cat-A | Cat-A | Cat-A | Cat-A | Cat-A | Cat-A |
|---|---|---|---|---|---|---|
| W/F, min. | 1.08 | 1.05 | 1.10 | 1.07 | 1.02 | 1.05 |
| Feed | CG | CFO | OHCUB | VGO | RCO | Mixed Feed: (CG:CFO:RCO) |
| Temp, ° C. | 580 | 580 | 580 | 580 | 580 | 580 |
| Yield wt % | | | | | | |
| Hydrogen | 0.07 | 0.24 | 0.23 | 0.25 | 0.48 | 0.22 |
| Dry gas | 5.23 | 8.82 | 12.26 | 14.65 | 13.51 | 12.28 |
| LPG | 35.82 | 39.15 | 43.23 | 40.49 | 36.38 | 34.76 |
| Gasoline (35-150° C.) | 50.17 | 12.78 | 15.75 | 11.12 | 13.03 | 14.7 |
| Heavy Naphtha (150-216° C.) | 3.82 | 6.2 | 7.8 | 5.46 | 5.67 | 5.76 |
| LCO (216-370° C.) | 2.23 | 17.35 | 9.51 | 11.02 | 12.78 | 11.16 |
| Gasoline + Total cycle oil, (35-370° C.) | 56.22 | 36.33 | 33.06 | 27.6 | 31.48 | 31.62 |
| CLO, (370° C.+) | 0.16 | 8.37 | 2.98 | 5.88 | 5.82 | 6.87 |
| Coke | 2.5 | 7.09 | 8.24 | 11.13 | 12.33 | 14.25 |
| 216° C. Conversion, wt % | 97.61 | 74.28 | 87.51 | 83.10 | 81.40 | 81.97 |
| Ethylene, wt % (part of Drygas) | 2.3 | 4.28 | 6.36 | 9.19 | 8.42 | 6.34 |
| Propylene, wt % (Part of LPG) | 17.53 | 19.18 | 21.42 | 20.42 | 15.19 | 16.18 |
| Ethylene in DG | 43.98 | 48.53 | 51.88 | 62.73 | 62.32 | 51.61 |
| Propylene in LPG | 48.94 | 48.99 | 49.55 | 50.43 | 41.75 | 46.56 |

Example-6: Cracking of VGO by Catalyst Composition B

This example illustrates, the working of catalyst B to crack VGO feed and the effect of reaction temperature on the output yield. Catalyst CAT-B was tested without metal and steamed at 810° C./5 hrs and its activity was evaluated in Fixed bed Auto MAT unit under ROT 580° C. and the products were analyzed as per the procedure mentioned above. Temperature is varied from 550° C. to 650° C. (Table 6). Propylene yield on fresh feed basis is higher at 580° C. i.e 27.63 wt % and ethylene yield on fresh feed basis is higher at 650° C. i.e. 14.67 wt %. However the maximum ethylene selectivity in dry gas is achieved at the temperature of 550° C. i.e. 74.62% and propylene selectivity in LPG could be achieved at 650° C. i.e. 62.51%.

TABLE 6

Cracking of VGO by CAT-B

| Catalyst | Cat-B | Cat-B | Cat-B | Cat-B |
|---|---|---|---|---|
| W/F, min. | 1.04 | 1.09 | 1.04 | 1.03 |
| Feed | VGO | VGO | VGO | VGO |
| Temp, ° C. | 550 | 580 | 600 | 650 |
| Yield wt % | | | | |
| Hydrogen | 0.2 | 0.23 | 0.25 | 0.36 |
| Dry gas | 13 | 15.52 | 19.51 | 27.34 |
| LPG | 45.42 | 50.38 | 46.29 | 34.52 |
| Gasoline (35-150° C.) | 12.56 | 9.67 | 9.51 | 9.16 |
| Heavy Naphtha (150-216° C.) | 7.62 | 5.03 | 6.02 | 7.01 |
| LCO (216-370° C.) | 12.88 | 9.88 | 8.65 | 8.17 |
| Gasoline + Total cycle oil, (35-370° C.) | 33.06 | 24.58 | 24.18 | 24.34 |
| CLO, (370° C.+) | 0.61 | 0.59 | 0.54 | 0.51 |
| Coke | 7.71 | 8.7 | 9.23 | 12.93 |
| 216° C. Conversion, wt % | 86.51 | 89.53 | 90.81 | 91.32 |
| Ethylene, wt % (Part of Drygas) | 9.7 | 10.28 | 11.99 | 14.67 |
| Propylene, wt % (part of LPG) | 24.6 | 27.63 | 25.11 | 21.58 |
| Ethylene in DG, % | 74.62 | 66.24 | 61.46 | 53.66 |
| Propylene in LPG, % | 54.16 | 54.84 | 54.24 | 62.51 |

Example-7: Vanadium Tolerance of the Catalyst-Additive System

This example illustrates the propylene selectivity of vanadium doped catalyst-additive system with respect to heavy feed stock. Catalyst CAT-A is metal doped as per the Mitchel method described in Example-4 and steam deactivated at 788° C./3 hrs. The feed stock with ~3 wt % CCR could increase propylene yield in the range of 8-12 wt % on fresh feed basis. It illustrates (Table 7), if the metal on the catalyst-additive mixture is 20000 ppm vanadium, then also the −216 conversion could be maintained more than 50 wt %. The ethylene selectivity in dry gas could be achieved around 34% and propylene selectivity in LPG could be achieved in the range of 45-50%.

Example-8: Ni & V Tolerance of the Catalyst-Additive System

This example illustrates the propylene selectivity of nickel and vanadium doped catalyst-additive system with respect to heavy feed stock. Catalyst CAT-C & CAT-D were metal doped as per the Mitchel method described in Example-4 and steam deactivated at 788° C./3 hrs. The feed stock with 10 wt % CCR could increase propylene selectivity in LPG by 49-50%. It illustrates (Table 8), if the metal on the catalyst-additive mixture is 10000 ppm nickel & 20000 ppm vanadium along with metal trap additive, then the −216 conversion could be maintained more than 60 wt %.

TABLE 8

Ni & V tolerance of CAT C and CAT D

| | Catalyst | | |
|---|---|---|---|
| | Cat-C Without metal | Cat-C | Cat-D |
| W/F, min. | 1.11 | 1.04 | 1.01 |
| Feed | Vacuum Residue | Vacuum Residue | Vacuum Residue |
| Temp, ° C. | 580 | 580 | 580 |
| Metal on catalyst, ppm | | | |
| Ni | Nil | 10000 | 10000 |
| V | Nil | 20000 | 20000 |
| Yield wt % | | | |
| Hydrogen | 0.48 | 0.17 | 0.24 |
| Dry gas | 13.51 | 6.41 | 6.75 |
| LPG | 32.38 | 11.05 | 12.86 |
| Gasoline, (C5-150° C.) | 13.03 | 24.81 | 25.09 |
| Heavy naphtha, (150-216° C.) | 5.67 | 5.26 | 4.74 |
| LCO, (216-370° C.) | 12.78 | 15.96 | 16.23 |
| Gasoline + Total cycle oil, (35-370° C.) | 43.48 | 46.03 | 46.06 |
| CLO, (370° C.+) | 5.82 | 20.03 | 19.73 |
| Coke | 16.37 | 16.31 | 14.36 |

TABLE 7

Vanadium Tolerance of CAT A and CAT B

| Catalyst | Cat-A | Cat-A | Cat-A | Cat-A | Cat-B |
|---|---|---|---|---|---|
| W/F, min. | 1.02 | 1.00 | 1.00 | 0.989 | 1.01 |
| Feed | Mixed feed (CG:CFO:RCO) | Mixed feed (CG:CFO:RCO) | Mixed feed (CG:CFO:RCO) | Mixed feed (CG:CFO:RCO) | Mixed feed (CG:CFO:RCO) |
| Temp, ° C. | 580 | 580 | 580 | 580 | 580 |
| Metal on the catalyst, V (ppm) | 5000 | 10000 | 15000 | 20000 | 15000 |
| Yield wt % | | | | | |
| Hydrogen | 0.53 | 0.6 | 0.78 | 0.78 | 0.52 |
| Dry gas | 9.46 | 8.92 | 8.17 | 7.43 | 7.17 |
| LPG | 27.15 | 23.58 | 19.55 | 17.87 | 17.01 |
| Gasoline, (C5-150° C.) | 15.8 | 13.18 | 12.74 | 8.32 | 9.84 |
| Heavy naphtha, (150-216° C.) | 6.07 | 5.23 | 4.73 | 3.29 | 3.45 |
| LCO, (216-370° C.) | 15.51 | 17.8 | 19.4 | 18.01 | 21.44 |
| Gasoline + Total cycle oil, (35-370° C.) | 37.38 | 36.21 | 36.87 | 29.62 | 34.73 |
| CLO, (370° C.+) | 10.98 | 15.69 | 19.13 | 28.21 | 24.97 |
| Coke | 14.5 | 15 | 15.5 | 16.09 | 15.6 |
| −216 conversion, wt % | 73.51 | 66.51 | 61.47 | 53.78 | 53.59 |
| Ethylene, wt % (part of Drygas) | 3.29 | 2.95 | 2.77 | 2.57 | 2.54 |
| Propylene, wt % (part of LPG) | 12.27 | 10.64 | 9.61 | 8.53 | 8.44 |
| Ethylene in DG, % | 34.78 | 33.07 | 33.9 | 34.59 | 35.43 |
| Propylene in LPG, % | 45.19 | 45.12 | 49.16 | 47.73 | 49.62 |

TABLE 8-continued

Ni & V tolerance of CAT C and CAT D

| | Catalyst | | |
|---|---|---|---|
| | Cat-C Without metal | Cat-C | Cat-D |
| −216° C. Conversion, wt % | 81.4 | 64.01 | 64.04 |
| Ethylene, wt (part of Drygas) | 6.13 | 2.4358 | 2.6379 |
| Propylene, wt % (part of LPG) | 8.22 | 5.45 | 6.49 |
| Propylene in LPG, % | 25.39 | 49.32 | 50.47 |
| Ethylene in DG, % | 45.37 | 38 | 39.08 |

Example 9: Working of Composite Catalyst Composition of Example 1

The effect of single particle composite catalyst as prepared in Example 1 is evaluated using VGO as the feed. The outcome of the same is given in Table 9.

TABLE 9

Cracking performance of composite catalyst as prepared in Example 1

| W/F, min. | 1.06 |
|---|---|
| Feed | VGO |
| Temp, ° C. | 580 |
| Yields, wt % | |
| Hydrogen | 0.18 |
| Dry gas | 13.95 |
| LPG | 40.91 |
| Gasoline (35-150° C.) | 12.82 |
| Heavy Naphtha (150-216° C.) | 6.42 |
| LCO (216-370° C.) | 9.63 |
| Gasoline + Total cycle oil (35-370° C.) | 30.67 |
| CLO, (370° C.+) | 4.54 |
| Coke | 11.55 |
| −216 Conversion, wt % | 85.83 |

TABLE 9-continued

Cracking performance of composite catalyst as prepared in Example 1

| Ethylene, wt % (part of Dry gas) | 7.99 |
|---|---|
| Propylene, wt % (part of LPG) | 22.44 |
| Ethylene in DG, % | 57.27 |
| Propylene in LPG, % | 54.85 |

Example-10: Comparative Example

This example illustrates the effect of variations in the catalyst composition on the cracking performance with VGO as the feed stock. Various catalysts compositions having the ingredients as indicated in Table 10 were prepared and tested without metal. The catalysts were steamed at 810° C./5 hrs and its activity was evaluated in Fixed bed Auto MAT unit under ROT 580° C. and the products were analyzed as per the procedure mentioned above.

TABLE 10

| CATALYST | E | B | F | G | H | I | J | K | L |
|---|---|---|---|---|---|---|---|---|---|
| W/F, min | 1.05 | 1.09 | 1.08 | 1.03 | 1.09 | 1.05 | 1.09 | 1.09 | 0.95 |
| Feed | VGO | VGO | VGO | VGO | VGO | VGO | VGO | VGO | VGO |
| Temp, ° C. | 580 | 580 | 580 | 580 | 580 | 580 | 580 | 580 | 580 |
| Y-zeolite | 25 | 24.5 | 10 | 12.5 | 15 | 8.75 | 21 | 19.25 | 14 |
| Pentasil zeolite | 8 | 8 | 7.5 | 6 | 3 | 6 | 6 | 6 | 16 |
| Residue up-gradation component | | 6.5 | 6.175 | 3.25 | 9.75 | 13 | 9.75 | 16.25 | 9.75 |
| Metal trap component | | 1.0 | 0.15 | 1.5 | 1.5 | 1.5 | 3.5 | 1.5 | 1.5 |
| Hydrogen | 0.26 | 0.23 | 0.16 | 0.21 | 0.23 | 0.21 | 0.18 | 0.23 | 0.25 |
| Dry gas | 15.56 | 15.52 | 11.93 | 11.44 | 13.38 | 14.28 | 13.45 | 12.96 | 14.90 |
| LPG | 42.47 | 50.38 | 39.42 | 38.48 | 41.4 | 38.20 | 38.71 | 37.57 | 40.49 |
| Gasoline (35-150° C.) | 12.53 | 9.67 | 16.98 | 17.32 | 14.78 | 16.31 | 13.32 | 13.66 | 11.12 |
| Heavy Naphtha (150-216° C.) | 5.17 | 5.03 | 8.43 | 7.85 | 7.16 | 7.61 | 6.72 | 6.14 | 5.45 |
| LCO (216-370° C.) | 8.98 | 9.88 | 10.21 | 11.46 | 10.60 | 11.75 | 10.63 | 11.88 | 11.02 |
| Gasoline + Total cycle oil (35-370° C.) | 26.68 | 24.58 | 35.62 | 36.63 | 32.54 | 35.67 | 30.67 | 31.68 | 27.59 |
| CLO, (370° C.+) | 4.42 | 0.59 | 3.53 | 4.33 | 3.97 | 3.95 | 5.44 | 6.24 | 5.88 |
| Coke | 10.61 | 8.7 | 9.34 | 8.92 | 8.48 | 7.65 | 11.99 | 11.57 | 11.13 |
| 216 Conversion, wt % | 86.60 | 89.53 | 86.26 | 84.21 | 85.43 | 84.30 | 83.93 | 81.88 | 83.10 |
| Ethylene, wt % part of Dry gas) | 10.04 | 10.28 | 6.38 | 5.85 | 7.96 | 9.21 | 7.61 | 7.08 | 9.19 |
| Propylene, wt % part of LPG) | 20.06 | 27.63 | 18.03 | 17.04 | 17.71 | 16.37 | 20.74 | 19.75 | 20.42 |
| Ethylene in DG, % | 64.52 | 66.24 | 53.48 | 51.14 | 59.49 | 64.50 | 56.58 | 54.63 | 61.68 |
| Propylene in LPG, % | 47.23 | 54.84 | 45.74 | 44.28 | 42.78 | 42.85 | 53.58 | 52.57 | 50.43 |

What claimed is:

1. A catalyst composition for use in a catalytic cracking process, said catalyst composition comprising 3.5 to 15.5% of pentasil zeolite, 9 to 40% of ultra-stable Y (USY) or rare earth exchanged USY (REUSY) zeolite, 3.5 to 15% of large pore active matrix based bottom up-gradation component and 0.3 to 3% of a metal trap component, the percentage being based on weight of the catalyst composition and wherein the large pore active matrix based bottom up-gradation component comprises 40-60 wt % alumina, 5-25 wt % silica, 20-60 wt % clay, 1-20 wt % $PO_4$ and has a pore size in the range of 80 Å to 200 Å.

2. The catalyst composition as claimed in claim 1, wherein the pentasil zeolite is in range of 4 to 8%, ultra-stable Y (USY) or rare earth exchanged USY (REUSY) zeolite is in the range of 10 to 25%, large pore active matrix based bottom up gradation component is in the range of 6 to 15% and metal trap component is in range of 0.4 to 3%.

3. The catalyst composition as claimed in claim 1, wherein the pentasil zeolite has a pore size in the range of 5.1 Å to 5.6 Å and is selected from a group comprising of ZSM-5 Zeolite, ZSM-11 Zeolite, ZSM-12 Zeolite, ZSM-22 Zeolite, ZSM-23 Zeolite, and ZSM-35 Zeolite.

4. The catalyst composition as claimed in claim 1, wherein the REUSY zeolite comprises of 3 to 5 wt. % of a rare earth cation selected from a group comprising of rhenium, lanthanum, cerium, praseodymium, neodymium, samarium and gadolinium.

5. The catalyst composition as claimed in claim 1, wherein the metal trap component
comprises at least one of a vanadium trap component and a nickel trap component wherein said vanadium trap component is selected from a group comprising of phosphorus, aluminium, lanthanum, cerium, rhenium, praseodymium, neodymium, samarium, gadolinium, tin, strontium, titanium, zirconium and silicon; and said nickel trap component is selected from a group comprising of cerium, antimony, bismuth, phosphorus, aluminium and silicon.

6. The catalyst composition as claimed in claim 1, wherein a remaining amount is comprised of a binder and filler.

7. The catalyst composition as claimed in claim 6, wherein the binder is selected from a group comprising of alumina, silica, silica-alumina and phosphate.

8. The catalyst composition as claimed in claim 6, wherein the filler is selected from a group comprising of kaolin clay, montmorillonite clay, bentonite clay, laolinite clay and halloysite clay, aluminum trihydrate, bayerite, and gamma alumina.

9. The catalyst composition as claimed in claim 1, wherein the catalyst composition is in the form of a composite catalyst or a mixture of additives.

* * * * *